(12) United States Patent
Hoeffkes et al.

(10) Patent No.: US 6,660,045 B1
(45) Date of Patent: Dec. 9, 2003

(54) HAIR COLORANT PREPARATION

(75) Inventors: Horst Hoeffkes, Duesseldorf (DE);
Bernd Meinigke, Leverkusen (DE);
Norbert Schettiger, Hilden (DE);
Konstantin Goutsis, Neuss (DE)

(73) Assignee: Henkel Kommanditgesellschaft auf Aktien (Henkel KGaA), Duesseldorf (DE)

( * ) Notice: Subject to any disclaimer, the term of this patent is extended or adjusted under 35 U.S.C. 154(b) by 0 days.

(21) Appl. No.: 09/581,039

(22) PCT Filed: Nov. 28, 1998

(86) PCT No.: PCT/EP98/07702

§ 371 (c)(1),
(2), (4) Date: Aug. 10, 2000

(87) PCT Pub. No.: WO99/29285

PCT Pub. Date: Jun. 17, 1999

(30) Foreign Application Priority Data

Dec. 8, 1997 (DE) .......................... 197 54 281

(51) Int. Cl.[7] .................................. A61K 7/13
(52) U.S. Cl. ...................... 8/405; 8/406; 8/407; 8/409; 8/410; 8/421; 8/512; 8/528
(58) Field of Search ............................. 8/405, 406, 409, 8/407, 410, 421, 512, 528

(56) References Cited

U.S. PATENT DOCUMENTS

| | | | |
|---|---|---|---|
| 4,650,865 A | 3/1987 | Lange et al. | 544/174 |
| 4,685,931 A | 8/1987 | Schieferstein et al. | 8/406 |
| 4,698,065 A | 10/1987 | Hoeffkes et al. | 8/406 |
| 4,780,310 A | * 10/1988 | Lang et al. | 8/406 |
| 4,822,598 A | * 4/1989 | Lang et al. | 8/405 |
| 5,114,428 A | 5/1992 | Hoeffkes et al. | 8/405 |
| 5,785,717 A | * 7/1998 | Maubry et al. | 8/409 |
| 5,891,199 A | * 4/1999 | Wachter et al. | 8/405 |
| 6,312,677 B1 | * 11/2001 | Millequant et al. | 424/70.17 |

FOREIGN PATENT DOCUMENTS

| | | |
|---|---|---|
| DE | 1 164 095 | 2/1964 |
| DE | 34 45 549 | 6/1986 |
| DE | 35 04 242 | 8/1986 |
| DE | 40 22 848 | 1/1992 |
| EP | 188 216 | 7/1986 |
| EP | 351 645 | 1/1990 |

OTHER PUBLICATIONS

Uber die Guerbetsche Reaktion und ihre technische Bedeutung, Angew. Chem. / 64.Jahrg.1952/Nr.8, p. 213–220.
Derwent WPIL Acc. No. 1992–033525[05].

* cited by examiner

Primary Examiner—Margaret Einsmann
Assistant Examiner—Eisa Elhilo
(74) Attorney, Agent, or Firm—Stephan D. Harper; Gergory M. Hill; Glenn E.J. Murphy

(57) ABSTRACT

The invention relates to a hair colorant comprised of a flowable, aqueous preparation of oxidation colorant intermediate products (A) and a flowable, aqueous oxidation agent preparation (B) which are mixed in a weight ratio A:B=1:2 to 2:1 to produce a gel-forming coloring batch immediately before applying on the hair. As supporting components in the oxidation colorant preparation, the hair colorant comprises 3.0 to 15 wt. % of a saturated or unsaturated, linear or branched alcohol with 8 to 36 C-atoms, 0.1 to 20 wt. % of a low-molecular water-soluble alcohol, 0.1 to 15 wt. % of a liquid fatty acid with 16 to 22 C-atoms in the form of a water-soluble soap, 0.1 to 20 wt. % of an addition product of 1 to 5 mole ethylene oxide on a linear fatty alcohol with 8 to 22 C-atoms and/or 0.1 to 15 wt. % of an optional alkoxylated amine. The oxidation agent preparation (B) preferably comprises 3 to 12 wt. % hydrogen peroxide, 0.1 to 5 wt. % of a water-soluble, synthetic tenside and 1 to 5 wt. % of a dispersed acrylic acid polymerizate or copolymerizate and/or methacrylic acid polymerizate or copolymerizate.

18 Claims, No Drawings

HAIR COLORANT PREPARATION

The invention relates to hair colorant preparations consisting of a flowable aqueous preparation of oxidation dye intermediates (A) and a flowable, aqueous oxidizing agent preparation (B), which are mixed directly prior to application to the hair to give a gel-like coloring mixture and which, following the mixing, are in the form of a pseudoplastic, flowable gel.

The carriers used for oxidation hair colorants are predominantly O/W creams or gels. The preparations of oxidation dye intermediates should, following the addition of the oxidizing agent, in most cases an aqueous hydrogen peroxide preparation, have a creamy or viscous gel-like consistency which permits easy application to and distribution on the hair, e.g. using a brush, and a certain adhesion to the hair, without the colorant running off the hair and wetting the scalp or face.

Oxidation dye preparations of the gel type usually have, as carriers, soaps in a mixture with water and lower alcohols or glycols. After mixing with aqueous oxidizing agent solutions, such preparations give viscous, gel-like coloring mixtures. A disadvantage is the formation of lime soaps when the colorant is rinsed out using hard water. A further disadvantage is that if the soap content is high the dye preparation becomes too viscous, but if the soap content is lower, the coloring mixture does not achieve the required viscosity. Also, the co-use of a synthetic surfactant which has a lime soap dispersing effect disturbs the formation of the flowable gel structure of the coloring mixture.

DE 40 22 848 A1 discloses a hair colorant preparation which aims to avoid the abovementioned disadvantages. The carrier system disclosed therein comprises soap, polyols, synthetic surfactants, and addition products of ethylene oxide with linear fatty alcohols and/or linear fatty alkylamines. However, upon application, this carrier system also exhibits disadvantages with regard to the conditioning action, and the viscosities are also relatively high.

The object of the present invention was, therefore, to find a carrier system suitable for the oxidizing colorants which, as well as having good conditioning properties, either does not have the abovementioned problems or exhibits them only to a significantly reduced extent.

It has been found that hair colorants consisting of a flowable, aqueous preparation of oxidation dye intermediates (A) and a flowable, aqueous oxidizing agent preparation (B), which are mixed together directly prior to application to the hair in the weight ratio A:B=1:2 to 2:1 to give a gel-like coloring mixture, have particularly good application properties when the preparation of oxidation dye intermediates (A) comprises, as carrier components,

| | |
|---|---|
| 6.0 to 15% by wt. | of a saturated or unsaturated, linear or branched alcohol having 8 to 36 carbon atoms, |
| 0.1 to 20% by wt. | of a low molecular weight water-soluble alcohol, |
| 0.1 to 15% by wt. | of a liquid fatty acid having 16 to 22 carbon atoms in the form of a water-soluble soap, |
| 0.1 to 20% by wt. | of an addition product of from 1 to 5 mol of ethylene oxide with a linear fatty alcohol having 8 to 22 carbon atoms and/or |
| 0.1 to 15% by wt. | of an amine according to the formula (I), |

-continued

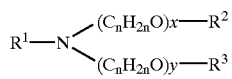

in which $R^1$ is a saturated or unsaturated alkyl radical having 8 to 22 carbon atoms, $R^2$ and $R^3$ independently of one another are hydrogen or an acyl group $R^4CO$, in which, in turn, $R^4$ is a $C_1$–$C_{21}$-alkyl or $C_2$–$C_{21}$-alkenyl group. n is 2 or 3, x and y independently of one another are a number from 0 to 5, with the proviso that the sum x + y = 2 to 6.

In a preferred embodiment it is also possible for

| | |
|---|---|
| 0.1 to 20% by wt. | of a polyol having 2 to 6 carbon atoms and/or |
| 0.5 to 10% by wt. | of a water-soluble, synthetic surfactant and/or |
| 0.1 to 10% by wt. | of a compound of the formula (II) $R^5$—$(OC_2H_4)x$—A—$(C_2H_4O)y$—$R^6$ (II) in which $R^5$ and $R^6$ are linear alkyl or alkenyl groups having 12 to 22 carbon atoms, x and y = 0 or 1, and A is an oxygen atom or an |

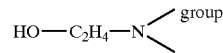

to be present.

The saturated or unsaturated, linear or branched alcohols having 8 to 36 carbon atoms to be used according to the invention are preferably fatty alcohols and/or Guerbet alcohols.

The term fatty alcohols means primary aliphatic alcohols of the formula (III)

$$R^7OH \qquad (III)$$

in which $R^7$ is an aliphatic, linear or branched hydrocarbon radical having 8 to 22 carbon atoms, which is saturated or can contain up to 3 double bonds.

Typical examples are 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoleyl alcohol, linolenyl alcohol, elaeostearyl alcohol, arachidyl alcohol, gadoleyl alcohol, behenyl alcohol, erucyl alcohol and brassidyl alcohol, and the technical-grade mixtures thereof which are produced, for example, during the high-pressure hydrogenation of technical-grade methyl esters based on fats and oils or aldehydes from the Roelen oxo synthesis, and as monomer fraction during the dimerization of unsaturated fatty alcohols.

Preference is given to technical-grade fatty alcohol mixtures having 12 to 18 carbon atoms, such as, for example, coconut, palm, palm kernel or tallow fatty alcohol, in particular coconut and/or tallow fatty alcohol.

The term Guerbet alcohols means alcohols prepared by alkaline condensation of alcohols to give higher molecular weight, branched isoalcohols. This reaction was first published by Guerbet in 1899. In 1952, Machemer described essential steps of the reaction (Angewandte Chemie 64

(1952) 213 20): As well as the dehydrogenation to give the ketone, in which hydrogen is cleaved off, and the aldol condensation, an important step in the course of the reaction is the crotonization, in which water is cleaved off. The reaction of the prior art is carried out at atmospheric pressure and a reaction temperature of from 240 to 260° C. The resulting branched alcohols are referred to as Guerbet alcohols. Since then, the prior art has disclosed a large number of other processes, according to which Guerbet alcohols can be obtained.

For the purposes of the present invention, the term lower molecular weight alcohols means water-miscible alcohols having 1 to 5 carbon atoms. These are preferably ethanol, propanol and/or isopropanol.

The fatty acids suitable for the formation of soap are preferably liquid or low-melting unsaturated linear $C_{16}$–$C_{22}$-fatty acids, such as palmitoleic acid, oleic acid, elaidic acid, petroselic acid, petroselaidic acid, gadoleic acid, erucic acid, brassidic acid, and mixtures of these fatty acids with one another and optionally with minor proportions of saturated linear fatty acids having 12 to 22 carbon atoms. Other fatty acids likewise suitable are branched fatty acids having 16 to 22 carbon atoms, e.g. 2-hexyldecanoic acid, isostearic acid and 2-octyldodecanoic acid.

To convert the fatty acids into water-soluble soaps, alkali metal hydroxides and alkali metal carbonates, ammonia, mono-, di- and trialkanolamines having 2 to 4 carbon atoms in the alkanol group, and alkaline amino acids, such as, for example, arginine, ornithine, lysine and/or histidine, are suitable.

Suitable as polyols having 2 to 6 carbon atoms are, for example, ethylene glycol, 1,2-propylene glycol, 1,3-propylene glycol, glycerol, erythritol, trimethylolpropane, diethylene glycol and dipropylene glycol. 1,2-propylene glycol is preferred.

Suitable water-soluble synthetic surfactants are preferably anionic, amphoteric, zwitterionic and nonionic surfactants with good solubility in water and a good lime-soap dispersibility. Such surfactants generally have a lipophilic linear alkyl or acyl group having 12 to 18 carbon atoms and a strongly dissociated ionic group or a nonionic polyether group which confers solubility in water. Suitable examples are sulfuric half-ester salts of linear fatty alcohols having 12 to 18 carbon atoms or of fatty alcohol polyglycol ethers having 12 to 16 carbon atoms in the alkyl group and 1 to 10 glycol ether groups. Other suitable anionic surfactants are, for example, linear alkanesulfonates and α-olefinsulfonates having 12 to 18 carbon atoms. Suitable nonionogenic surfactants are, for example, the addition products of from 7 to 30 mol of ethylene oxide with linear fatty alcohols having 12 to 18 carbon atoms, with fatty acids having 12 to 18 carbon atoms, and with fatty acid monoglycerides and with fatty acid sorbitan monoesters. Preferably, suitable nonionogenic surfactants are the fatty alkylamine oxides and, in particular, the fatty alkyl glycosides, preferably fatty alkyl glucosides. The fatty alkyl group can have 12 to 18 carbon atoms in said products. For the purposes of the present invention, particular preference is also given to amphoteric surfactants, such as, for example, N-fatty alkyldimethylglycine or N-fatty alkylaminopropionic acid and/or zwitterionic surfactants, e.g. N-fatty alkyldimethylammonium glycinate or N-fatty acylaminopropyldimethyl glycinate.

Preference is also given to cationic surfactants, such as quaternary ammonium compounds (QAC), in particular quaternized trialkylammonium compounds containing alkyl radicals of chain length from C8 to C22.

It has been found that the addition of further nonionogenic surfactants of limited solubility in water achieves a thickening of the oxidation colorant preparation and, in particular, of the coloring mixture prepared directly prior to application.

Suitable addition products of 1 to 5 mol of ethylene oxide with linear fatty alcohol having 12 to 22 carbon atoms are all adducts obtainable by the known industrial oxyethylation processes. Preference is given to the addition products which contain only a little free fatty alcohol and have a narrowed homolog distribution (so-called "narrow range ethoxylates"), as are accessible, for example, according to the process described in DE 38 43 713 A1.

Suitable addition products of from 1 to 4 mol of ethylene oxide with a linear fatty alkylamine having 12 to 22 carbon atoms are all adducts obtainable by known industrial processes, which are also available commercially. The addition product of 2 mol of ethylene oxide with a $C_{12}$–$C_{18}$-cocoalkylamine is particularly suitable.

Suitable compounds of the formula $$R^5\text{—}(OC_2H_4)_x\text{—}A\text{—}(C_2H_4O)_y\text{—}R^6 \quad\quad (II)$$

in which A is an oxygen atom, are dialkyl ethers having 12 to 18 carbon atoms in the alkyl groups. Such products are known in the literature. Even better suited are the products of the formula II in which x or y or both=1. Such dialkyl oxyethyl ethers can be prepared by esterification processes known in the literature from fatty alcohols and fatty alkyl oxyethanols. The products of the formula II in which A is an

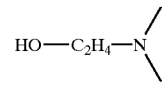

group can be obtained, for example, from triethanolamine by O-alkylation with 2 mol of a sulfuric half-ester salt of a $C_{12}$–$C_{22}$-fatty alcohol according to the process for the preparation of ether amines described in DE 35 04 242.

Particularly preferred compounds of the formula II are, for example, dicetylstearyl ether, dicetylstearyl dioxyethyl ether and N,N-bis(2-cetylstearyl-oxyethyl)aminoethanol.

While the use of addition products of 1 to 5 mol of ethylene oxide with a linear fatty alcohol achieves the required thickening in most cases by virtue of this component alone, in the case of the use of addition products of 1 to 4 mol of ethylene oxide with a linear fatty alkylamine, it may be advantageous to use these in combination with 1 to 10% by weight of a compound of the formula II. In this connection, efforts are made for the preparation of oxidation dye intermediates (A) to have a viscosity of at most 1 Pas (20° C.), and the coloring mixture which forms by mixing (A) with the oxidizing agent preparation (B) to have a viscosity of at least 10 Pas (20° C.) (viscosity measurement using a Brookfield rotational viscometer, model RTV, spindle 4, 4 rpm).

Moreover, the preparation of oxidation dye intermediates (A) of course contains the oxidation dye intermediates which form the dye in the presence of oxidizing agents, and optionally also direct dyes. Suitable oxidation dye intermediates are, for example, the known color bases or developer compounds and known modifiers or coupler compounds. The oxidation dyes form as a result of oxidative coupling of one or more developer components with one another or with one or more coupler components in the presence of an oxidizing agent. The developer components used are usually primary aromatic amines having a further free or substituted hydroxyl or amino group in the para or ortho position, diaminopyridine derivatives, heterocyclic hydrazones, 4-aminopyrazolone derivatives, and 2,4,5,6-tetraaminopyrimidine and derivatives thereof.

Typical examples are p-phenylenediamine, p-toluylenediamine, p-aminophenol, 1-(β-hydroxyethyl)-2,5-diaminobenzene, N,N-bis(2-hydroxyethyl)-p-phenylenediamine, 2-(2,5-diaminophenoxy)ethanol, 4,5-diamino-1-(2-hydroxyethyl)pyrazole, 1-phenyl-3-carboxyamido-4-amino-5-pyrazolone, 4-amino-3-methylphenol, 2-hydroxymethyl-4-aminophenol, 2-aminomethyl-4-aminophenol, 2,4,5,6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2-hydroxyethylaminomethyl-4-aminophenol, 1,3-bis[N-(2-hydroxyethyl)-N-(4-aminophenyl)amino]-2-propanol, and 4,4'-diaminodiphenylamine. For the purposes of the present invention, preferred developer components are 1,3-bis[N-(2-hydroxyethyl)-N-(4-aminophenyl)amino]-2-propanol, 6-chloro-2-aminophenol, 1,10-bis(2,5-diaminophenyl)-1,4,7,10-tetraoxadecane; particular preference is given to using 6-hydroxy-2,4,5-triaminopyrimidine, 2-(2,5-diaminophenyl)ethanol, 2,6-dichloro-4-aminophenol, 3-methyl-4-aminophenol, 2,4,5,6-tetraaminopyrimidine, 2-aminomethyl-4-aminophenol and 2-hydroxymethyl-4-aminophenol.

The coupler components usually used are m-phenylenediamine derivatives, naphthols, resorcinol and resorcinol derivatives, pyrazolones and m-aminophenols. Suitable coupler substances are, in particular 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis(2,4-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol, 2,5-dimethylresorcinol, 2,6-dihydroxypyridine, 2,6-diaminopyridine, 2,6-dihydroxy-3,4-dimethylpyridine, 2,6-dihydroxy-4-methylpyridine, 3-amino-2-methylamino-6-methoxypyridine, 2,6-bis(2-hydroxyethylamino)toluene, 2,4-diaminophenoxyethanol and 2-amino-4-hydroxyethylaminoanisole. For the purposes of the present invention, preference is given to using the following coupler substances: 2,4-diaminophenoxyethanol, 2-methylresorcinol, 1,3-bis(2,4-diaminophenoxy)propane, 2,7-dihydroxynaphthalene, α-naphthol, 2,6-dihydroxy-3,4-dimethylpyridine, 1,5-dihydroxynaphthalene, 5-amino-2-methylphenol, 2-amino-4-(β-hydroxyethylamino)anisole, 3-amino-2-chloro-6-methylphenol and 5-amino-4-chloro-2-methylphenol. Particular preference is given to 2,4-diaminophenoxyethanol, 1,3-bis(2,4-diaminophenoxy)propane, 2-methylresorcinol, 2,7-dihydroxynaphthalene and 2,6-dihydroxy-3,4-dimethylpyridine.

Moreover, the preparation of oxidation dye intermediates (A) can contain suitable additives for stabilizing the dye intermediates; these are complexing agents, e.g. ethylenediaminotetraacetic acid, nitrilotriacetic acid, 1-hydroxyethane-1,1-diphosphonic acid or other organo-diphosphonic acids in the form of their alkali metal salts, antioxidants, such as, for example, sodium sulfite, sodium bisulfite, hydroquinone or salts of thioglycolic acid or ascorbic acid, buffer salts, such as, for example, ammonium sulfate, ammonium carbonate, ammonium citrate, and ammonia or an alkanolamine to set a pH of from 8 to 10.

In a preferred embodiment, the preparations of oxidation dye intermediates (A) according to the invention comprise direct dyes, which include customary direct dyes, e.g. from the group of nitrophenylenediamines, nitroaminophenols, azo dyes, anthraquinones or indophenols, such as, for example, compounds known under the international names or trade names HC Yellow 2, HC Yellow 4, HC Yellow 6, Basic Yellow 57, Disperse Orange 3, HC Red 3, HC Red BN, Basic Red 76, HC Blue 2, Disperse Blue 3, Basic Blue 99, HC Violet 1, Disperse Violet 1, Disperse Violet 4, Disperse Black 9, Basic Brown 16 and Basic Brown 17, and 4-amino-2-nitrodiphenylamine-2'-carboxylic acid, e 6-nitro-1,2,3,4-tetrahydroquinoxaline, hydroxyethyl-2-nitrotoluidine, picramic acid, 2-amino-6-chloro-4-nitrophenol and 4-N-ethyl-1,4-bis(2'-hydroxyethylamino)-2-nitrobenzene hydrochloride in an amount of from 0.01 to 20% by weight, based on the total oxidation hair colorant. 4-Amino-2-nitrodiphenylamine-2'-carboxylic acid, 6-nitro-1,2,3,4-tetrahydroquinoxaline and HC Red BN are particularly preferred direct dyes according to the invention.

In a preferred embodiment, is also possible for indoles and/or indolines to be present. For the purposes of the present invention, particular preference is given to 6-hydroxyindole, N-methyl-6-hydroxyindole, N-ethyl-6-hydroxyindole, N-propyl-6-hydroxyindole, N-butyl-6-hydroxyindole, 4-hydroxyindole, N-methyl-4-hydroxyindole, N-ethyl-4-hydroxyindole, N-propyl-4-hydroxyindole, N-butyl-4-hydroxyindole, 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, and 5,6-dihydroxyindoline, N-methyl-5,6-dihydroxyindoline, N-ethyl-5,6-dihydroxyindoline, N-propyl-5,6-dihydroxyindoline and N-butyl-5,6-dihydroxyindoline.

Furthermore, the preparations according to the invention can also comprise naturally occurring dyes, such as, for example, henna red, henna neutral, henna black, camomile blossom, sandalwood, black tea, buckthorn bark, sage, logwood, madder root, catechu, sedre and alkanna root.

In addition, polymers, for example zwitterionic and/or nonionic polmers, such as silicone oils, preferably cationic polymers such as Polymer JR 400, Merquat 100, Gafquat 734, Gafquat 755, Mirapol A15, hexadimethrine chloride (condensation of N,N,N',N'-tetramethyl-hexamethylenediamine and trimethylene chloride) and polyquaternium-34, may be present.

Particular preference is given to preparations of oxidation dye intermediates (A) which comprise proteins and/or protein derivatives of vegetable or animal origin, such as, for example, pea, soya, wheat and almond protein hydrolyzate or acacia protein, and collagen and keratin hydrolyzate.

Preferred thickeners according to the invention are xanthan gum, agar agar, linear and crosslinked polyacrylates, nonionogenic and anionic cellulose derivatives.

Furthermore, hair cosmetic auxiliaries may be present, in particular bisabolol, plant extracts, vitamins such as, preferably, niacin amide, tocopherol, vitamin A, biotin and vitamin D.

The oxidizing agent preparation (B) particularly preferably comprises

| | |
|---|---|
| 3 to 12% by wt. | of hydrogen peroxide |
| 0.1 to 5% by wt. | of a water-soluble, synthetic surfactant and |
| 1 to 5% by wt. | of a dispersed acrylic acid and/or methacrylic acid polymer or copolymer | in the aqueous carrier, in addition to the stabilizing auxiliaries customary in such preparations. In the simplest case, however, it can also consist of water alone, so that the oxidation is brought about by the atmospheric oxygen. The prior art also discloses a number of catalysts, such as, for example, salts of copper, manganese, iron, cerium, lanthanum, vanadium, molybdenum and tungsten, which can be added to the reaction mixture in the case of oxidation by atmospheric oxygen. As is known from the prior art, there are also other oxidation options, for example using iodide/periodate and/or iodate or in combination of iodide with hydrogen peroxide, and also enzymatically. For the purposes of the present invention, all oxidation methods known from the literature are suitable, meaning that the oxidizing agent preparation (B) can comprise the corresponding substances.

The water-soluble synthetic surfactants which can be used in the oxidizing agent preparation (B) are the anionic, amphoteric, zwitterionic and nonionic surfactants, or mixtures thereof, which have already been given for the preparation of oxidation dye intermediates (A). Preference is given to using anionic surfactants, e.g. sulfuric half-ester salts of linear fatty alcohols having 12 to 18 carbon atoms or of fatty alcohol polyglycol ethers having 12 to 16 carbon atoms in the alkyl group and 1 to 10 glycol ether groups in the form of their alkali metal, magnesium, ammonium or alkanolammonium salts.

The oxidizing agent preparation (B) further preferably comprises complexing agents and buffer salts to set a pH of from 2 to 5. In this weakly acidic medium, the acrylic acid and/or methacrylic acid polymer dispersions remain thinly liquid and stable. Upon mixing with the alkaline preparation of oxidation dye intermediates (A), which comprises ammonia and buffer salts to set a pH of from 8 to 10, the pH of the mixture increases and the carboxyl groups of the polymer or copolymer are converted into the salt form. During this operation, the polymers begin to dissolve in the aqueous medium and to increase the viscosity of the solution.

A particularly favorable feature for the viscosity buildup following the mixing of the preparation of oxidation dye intermediates (A) and the oxidizing agent preparation (B) is the content of dispersed acrylic acid and/or methacrylic acid polymer or copolymer in (B). Such dispersions of copolymers, e.g. comprising at least 10% by weight of acrylic acid lower alkyl ester, 25 to 70% by weight of methacrylic acid and optionally up to 40% by weight of a further comonomer, are described, for example, in GB 870 994. DE 11 64 095 discloses mixed polymers comprising 50 to 75% by weight of ethyl acrylate, 25 to 35% by weight of acrylic acid and 0 to 25% by weight of other comonomers. Suitable dispersions of this type are available commercially, e.g. under the trade name Latekoll® D (BASF). The copolymers comprising 50 to 60% by weight of ethyl acrylate, 30 to 40% by weight of methacrylic acid and 5 to 15% by weight of acrylic acid, crosslinked with ethylene glycol dimethacrylate, which are described in DE 34 45 549 are particularly suitable.

The examples below serve to illustrate the subject-matter of the invention in more detail:

EXAMPLES

The following preparations of oxidation dye intermediates (A) were tested (all data in % by weight):

TABLE 1

| Raw material | Formulations | | | | | |
| --- | --- | --- | --- | --- | --- | --- |
| | 1 | 2 | 3 | 4 | 5 | 6 |
| Oleic acid | 6.75 | 6.75 | 6.75 | 6.75 | 6.75 | 6.75 |
| Lorol ® (technical-grade)[1] | 6.75 | 6.75 | 6.75 | 6.75 | 6.75 | — |
| Texapon ® NSW[2] | 3.95 | 3.95 | 3.95 | 3.95 | 3.95 | 3.95 |
| Plantasol ® W 20[3] | 3.0 | 3.0 | 3.0 | 3.0 | 3.0 | 3.0 |
| Dehydol ® LS-2[4] | — | 13.5 | 6.75 | — | — | 13.5 |
| Cocamine 2 EO | — | — | — | 6.75 | — | — |
| Lowenol ® S 216[5] | — | — | — | — | 6.75 | — |
| 1,2-Propylene glycol | 6.75 | 6.75 | 6.75 | 6.75 | 6.75 | 6.75 |
| Isopropyl alcohol | 15.0 | 15.0 | 15.0 | 15.0 | 15.0 | 15.0 |
| Monoethanolamine | 5.0 | 5.0 | 5.0 | 5.0 | 5.0 | 5.0 |
| Arginine | 1.0 | 1.0 | 1.0 | 1.0 | 1.0 | 1.0 |
| Na metabisulfite | 0.2 | 0.2 | 0.2 | 0.2 | 0.2 | 0.2 |
| Ascorbic acid | 0.2 | 0.2 | 0.2 | 0.2 | 0.2 | 0.2 |
| Perfume oil | 0.5 | 0.5 | 0.5 | 0.5 | 0.5 | 0.5 |
| Resorcinol | 0.06 | 0.06 | 0.06 | 0.06 | 0.06 | 0.06 |
| p-Aminophenol hydrochloride | 0.06 | 0.06 | 0.06 | 0.06 | 0.06 | 0.06 |
| p-Toluylenediamine sulfate | 0.05 | 0.05 | 0.05 | 0.05 | 0.05 | 0.05 |
| Water | ad 100 | | | | | |

[1]C12/C18-fatty alcohol (100% by weight of active substance)
[2]C12/C14-fatty alcohol 2EO sulfate, sodium salt (25% by weight of active substance in aqueous solution)
[3]Wheat protein hydrolyzate (20% by weight of active substance in aqueous solution)
[4]C12/C14-fatty alcohol 2EO (100% by weight of active substance)
[5]Bis(2-hydroxyethyl)soyaalkylamine dioleate (97% by weight of active substance)

The preparations of oxidation dye intermediates (A) listed in Table 1, formulations 1 to 5, were then mixed with the oxidizing agent preparation (B), formulation 7, listed below (Table 2) in the ratio 4:5. The viscosity of the resulting gels was then determined.

TABLE 2

| Raw material | Formulation 7 amount in % by wt. |
| --- | --- |
| Hydrogen peroxide | 5.0 |
| Texapon ® NSW[2] | 2.0 |
| Acrysol ® 33[6] | 5.5 |
| Turpinal ® SL[7] | 1.5 |
| Ammonia, 25% strength by wt. aqueous solution | 0.65 |
| Water | ad 100 |

[6]Acrylate copolymer (30% by weight of active substance)
[7]Acetophosphonic acid (60% by weight of active substance)

The viscosity was measured at 20° C. using a Brookfield rotational viscometer, model RTV, spindle 4, 4 revolutions per minute. The results are given in Table 3:

TABLE 3

| Formulation | Viscosity [mPas] |
| --- | --- |
| 1 + 7 | 1975 |
| 2 + 7 | 18000 |
| 3 + 7 | 11250 |
| 4 + 7 | 10500 |
| 5 + 7 | 12500 |

To determine the conditioning properties of the formulations according to the invention, formulations 2 and 6 were compared. For this, the two formulations were mixed with formulation 7 as described above, and then 4 g of each mixture was applied in each case to a hair swatch (2 g) and, after a contact time of 30 minutes, the combability was evaluated subjectively (using a fine-toothed, serrated hard rubber comb). The results are given in Table 4.

TABLE 4

| Formulation | Combability* |
|---|---|
| Hair swatch before coloring | 5 |
| Following treatment with 2 + 7 | 2 |
| Following treatment with 6 + 7 | 4 |

*The combability was assessed subjectively using a grade scale from 1 - very good to 5 = poor.

What is claimed is:

1. A hair colorant comprising a flowable preparation of oxidation dye intermediates (A) and a flowable, aqueous oxidizing agent preparation (B), which are mixed together directly prior to application to the hair in the weight ratio A:B=1:2 to 2:1 to give a coloring mixture with a flowable gel structure, wherein the preparation of oxidation dye intermediates (A) has a viscosity of 1 Pas or less at 20° C. and comprises, as carrier components,
   (i) 6.0% to 15% by weight of a saturated or unsaturated, linear or branched alcohol having 8 To 36 carbon atoms,
   (ii) 0.1% to 20% by weight of a low molecular weight water-soluble monoalcohol,
   (iii) 0.1% to 15% by weight of a liquid fatty acid having 16 to 22 carbon atoms in the form of 4 water-soluble soap, and
   (iv) 0. 1% to 20% by weight of a nonionic addition product of 1 to 5 moles of ethylene oxide with a linear fatty alcohol having 8 to 22 carbon atoms; and
   wherein The viscosity of the preparation of oxidation dye intermediates (A) and aqueous oxidizing agent preparation (B) after combination is at least 10 Pas at 20°, wherein the viscosities are measured with an RTV Brookfield viscometer, spindle number 4 at 4 rpm.

2. The hair colorant of claim 1, wherein the preparation of oxidation dye intermediates (A) comprises technical-grade fatty alcohols having 12 to 18 carbon atoms.

3. The hair colorant of claim 1, which further comprises 0.1 to 15% by wt. of an amine according to the formula (I), $$R^1-N \begin{cases} (C_nH_{2n}O)x-R^2 \\ (C_nH_{2n}O)y-R^3 \end{cases} \quad (I)$$

in which $R^1$ is a saturated or unsaturated alkyl radical having 8 to 22 carbon atoms, $R^2$ and $R^3$ independently of one another are hydrogen or an acyl group $R^4CO$, in which, in turn, $R^4$ is a $C_1-C_{21}$-alkyl or $C_2-C_{21}$-alkenyl group. n is 2 or 3, x and y are a number from 0 to 5, with the proviso that the sum x+y=2 to 6].

4. The hair colorant of claim 1, wherein the preparation of oxidation dye intermediates (A) comprises a polyol.

5. The hair colorant of claim 1, wherein the preparation of oxidation dye intermediates (A) comprises a water-soluble synthetic surfactant selected from the group consisting of cationic, amphoteric, and zwitterionic surfactants and fatty alkyl glycosides.

6. The hair colorant of claim 1, wherein the preparation of oxidation dye intermediates (A) comprises dicetylstearyl ether, dicetylstearyl oxyethyl ether, dicetylstearyl dioxyethyl ether, N,N-bis(2-cetylstearyl-oxyethyl)aminoethanol, or a mixture thereof.

7. The hair colorant of claim 1, wherein the preparation of oxidation dye intermediates (A) comprises a developer substance selected from the group consisting of 1,3-bis(N-(2-hydroxyethyl)-N-(4-aminophenyl)amino)-2-propanol, 6-chloro-2-aminophenol, 1,10-bis(2,5-diaminophenyl)-1,4,7,10-tetraoxadecane, 6-hydroxy-2,4,5-triaminopyrimidine, 2-(2,5-diaminophenyl)-ethanol, 2,6-dichloro-4-aminophenol, 3-methyl-4-aminophenol, 2,4,5,6-tetraaminopyrimidine, 2-aminomethyl-4-aminophenol, and 2-hydroxymethyl-4-aminophenol.

8. The hair colorant of claim 1, wherein the preparation of oxidation dye intermediates (A) comprises a coupler substance selected from the group consisting of 2,4-diaminophenoxyethanol, 2-methylresorcinol, 1,3-bis(2,4-diaminophenoxy)propane, 2,7-dihydroxynaphthalene, α-naphthol, 2,6-dihydroxy-3,4-dimethylpyridine, 1,5-dihydroxynaphthalene, 5-amino-2-methylphenol, 2-amino-4-(β-hydroxyethylamino)-anisole, 3-amino-2-chloro-6-methylphenol, and 5-amino-4-chloro-2-methylphenol.

9. The hair colorant of claim 1, wherein the preparation of oxidation dye intermediates (A) comprises a protein or protein hydrolyzate selected from the group consisting of pea, soya and almond protein hydroxyzates, acacia protein, and collagen and keratin hydrolyzate.

10. The hair colorant of claim 1, wherein the preparation of oxidation dye intermediates (A) comprises a cationic polymer chosen from the group formed by Polymer JR 400, Merquat 100, Gafquat 734, Gafquat 755, Mirapol A15, hexadimethrine chloride, and polyquaternium 34.

11. The hair colorant of claim 1, wherein the oxidizing agent preparation (B) comprises
   3 to 12% by wt. of hydrogen peroxide
   0.1 to 5% by wt. of a water-soluble, synthetic surfactant, and
   1 to 5% by wt. of a dispersed acrylic acid or methacrylic acid polymer or copolymer or a mixture thereof.

12. The hair colorant of claim 2, wherein the technical-grade fatty alcohols are coconut, palm, palm kernel, or tallow alcohols.

13. The hair colorant of claim 1, wherein the saturated or unsaturated, linear or branched alcohol comprises 12 to 36 carbon atoms.

14. A hair colorant comprising a flow able preparation of oxidation dye intermediates (A) and a flowable, aqueous oxidizing agent preparation (B), which are mixed together directly prior to application to the hair in the weight ratio A:B=1:2 to 2:1 to give a coloring mixture with a flowable gel structure,
   wherein the preparation of oxidation dye intermediates (A) comprises, as carrier components
      (i) 6.0% to 150% by weight of a saturated or unsaturated, linear or branched alcohol having 8 to 36 carbon atoms,
      (ii) 0.1% to 20% by weight of a low molecular weight water-soluble monoalcohol,
      (iii) 0.1% to 15% by weight of a liquid fatty acid having 16 to 22 carbon atoms in the form of a water-soluble soap, and
      (iv) 0.1% to 20% by weight of a nonionic addition product of 1 to 5 moles of ethylene oxide with a linear fatty alcohol having 8 to 22 carbon atoms;
   wherein the aqueous oxidizing agent preparation (B) comprises water, hydrogen peroxide and at least one dispersed acrylic acid polymer or copolymer, or methacrylic polymer or copolymer or a mixture thereof; and
   wherein the viscosity of the preparation of oxidation dye intermediates (A) and the aqueous oxidizing agent preparation (B) after combination is at least 10 Pas at 20° C., wherein the viscosity is measured with an RTV Brookfield viscometer, spindle number 4 at 4 rpm.

15. The hair colorant of claim 14 wherein the preparation of oxidation dye intermediates (A) has a viscosity of 1 Pas or less.

16. The hair colorant of claim 15 further comprising from 0.1% to 15% by weight of an amine according to the formula (I),

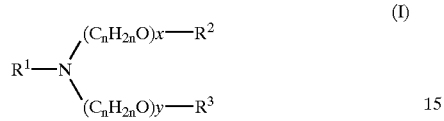

(I)

in which $R^1$ is a saturated or unsaturated alkyl radical having 8 to 22 carbon atoms, $R^2$ and $R^3$, independently of one another, are hydrogen or an acyl group $R^4CO$, where $R^4$ is a $C_1$–$C_{21}$-alkyl or $C_2$–$C_{21}$-alkenyl group, n is 2 or 3, and x and y are a number from 0 to 5, with the proviso that the sum x+y=2 to 6.

17. The hair colorant of claim 14, wherein the preparation of oxidation dye intermediates (A) her comprises a polyol.

18. The hair colorant of claim 14, wherein the oxidizing agent preparation (B) comprises:

from 3% to 12% by weight of the hydrogen peroxide from 0.1% to 5% by weight of a water-soluble, synthetic surfactant, and from 1% to 5% by weight of the dispersed acrylic acid or methacrylic acid polymer or copolymer or a mixture thereof.

* * * * *

UNITED STATES PATENT AND TRADEMARK OFFICE
CERTIFICATE OF CORRECTION

PATENT NO. : 6,660,045 B1
DATED : December 9, 2003
INVENTOR(S) : Hoeffkes et al.

It is certified that error appears in the above-identified patent and that said Letters Patent is hereby corrected as shown below:

Column 9,
Line 21, delete "To", and insert therefore -- to --.
Line 27, delete "4", and insert therefore -- a --.
Line 32, delete "The", and insert therefore -- the --.
Line 54, after "group", delete ".".
Line 55, after "6", delete "]".

Column 10,
Line 52, delete "150%", and insert therefore -- 15% --.

Column 12,
Line 6, delete "her", and insert therefore -- further --.

Signed and Sealed this

Nineteenth Day of October, 2004

JON W. DUDAS
*Director of the United States Patent and Trademark Office*